United States Patent [19]

Martin et al.

[11] 4,111,967

[45] Sep. 5, 1978

[54] SILICON CONTAINING CATALYSTS

[75] Inventors: Manfred Martin, Cologne; Walter Schmidt; Gerhard Scharfe, both of Leverkusen, all of Germany

[73] Assignee: Bayer Aktiengesellschaft, Leverkusen, Germany

[21] Appl. No.: 759,222

[22] Filed: Jan. 13, 1977

Related U.S. Application Data

[62] Division of Ser. No. 624,499, Oct. 21, 1975, abandoned.

[30] Foreign Application Priority Data

Nov. 9, 1974 [DE] Fed. Rep. of Germany ....... 2453232

[51] Int. Cl.$^2$ .............................................. C07C 49/66
[52] U.S. Cl. ................................ 260/396 R; 252/439; 260/346.4; 260/599; 260/687 R; 568/771
[58] Field of Search ................ 260/346.4, 396 R, 599, 260/621 G, 687 R; 252/439

[56] References Cited

U.S. PATENT DOCUMENTS

| | | | |
|---|---|---|---|
| 2,973,371 | 2/1961 | Chomitz et al. | 260/346.4 |
| 3,183,196 | 5/1965 | Watanabe et al. | 252/456 X |
| 3,186,794 | 6/1965 | Davies | 252/456 X |
| 3,407,215 | 10/1968 | Egbert et al. | 60/346.4 |
| 3,870,730 | 3/1975 | Scharfe et al. | 260/369 |
| 4,032,548 | 6/1977 | Martin et al. | 260/396 R |

FOREIGN PATENT DOCUMENTS 798,181   4/1973   Belgium.

*Primary Examiner*—Richard L. Raymond
*Attorney, Agent, or Firm*—Burgess, Dinklage & Sprung

[57] ABSTRACT

Catalysts for the catalytic oxidation of organic compounds containing silicon, vanadium, sulfur, oxygen and at least one alkali metal element. The catalyst is prepared from a silicic acid which has an average particle size of less than 50 microns and an alkali metal content of less than 2% by weight, calculated as $Na_2O$ and expressed relative to anhydrous silicic acid.

10 Claims, No Drawings

SILICON CONTAINING CATALYSTS

This is a division of application Ser. No. 624,499, filed Oct. 21, 1975, now abandoned.

BACKGROUND

The present invention relates to a catalyst containing the elements silicon, vanadium, sulphur and oxygen and at least one alkali metal element, a process for its preparation and its use in the oxidation of organic compounds with molecular oxygen.

Catalysts which contain the elements silicon, vanadium, sulphur and oxygen and at least one alkali metal are known in principle and are described, for example, in Fiat Report 649, London, 1947, page 2 to 3. According to this Report, they are prepared by treating potassium waterglass with sulphuric acid, drying the silicic acid thus obtained and subsequently impregnating it with a solution of a vanadyl compound, and subsequent shaping. The abovementioned publication furthermore discloses that the catalysts containing the elements silicon, vanadium, sulphur and oxygen and at least one alkali metal element can be used for the oxidation of naphthalene with molecular oxygen to give phthalic anhydride. In addition, Belgian Pat. No. 798,181 discloses that the catalysts containing the elements silicon, vanadium, sulphur and oxygen and an alkali metal can be employed for the oxidation of naphthalene with oxygen to give naphthoquinone.

SUMMARY

According to the present invention there is provided a catalyst containing the elements silicon, vanadium, sulphur and oxygen and at least one alkali metal element which has been prepared using a silicic acid of average particle size less than 50 micron and having an alkali metal content less than 2% by weight, calculated as $Na_2O$ and expressed relative to anhydrous silicic acid.

DESCRIPTION

Catalysts into which 90 to 100% of the total silicon present in the catalyst have been introduced by using a silicic acid of average particle size less than 50 micron and of alkali metal content less than 2% by weight, calculated as $Na_2O$ and expressed relative to anhydrous silicic acid, have proved particularly advantageous.

The silicic acid used for the catalyst according to the invention is in general prepared by precipitation from an alkali metal waterglass with the aid of a mineral acid, for example from sodium waterglass or potassium waterglass by means of sulphuric acid. The method of carrying out this precipitation of silicic acid is known (see, in this context, also Fiat Report 649, London, 1947, pages 2-3). The silicic acid thus obtained is then freed from alkali, by washing with water, to the point that the alkali content, calculated as $Na_2O$ and expressed relative to anhydrous silicic acid, is less than 2% by weight. The silicic acid, which has in this way largely been freed from alkali by washing, is dried in a conventional manner, complete removal of the water not being necessary; thus it is possible to employ a silicic acid which contains between 0 and 20% by weight of water. The requisite average particle size of less than 50 micron can be achieved either by adjusting the precipitation conditions or by grinding the precipitated and dried silicic acid in a manner which is in itself known. Silicic acids of average particle size in the range from 10 to 30 micron are preferred. The internal surface area (by the BET method) of the silicic acid used according to the invention is in general from about 50 to 300 $m^2/g$, silicic acids of internal surface area of from 100 to 200 $m^2/g$ being preferred. The silicic acid may contain small amounts of impurities such as, for example, aluminum, iron or sulphur, occasioned by the starting materials used for its preparation. Thus, it will in general contain up to 1% by weight of aluminum, calculated as $Al_2O_3$, up to 0.5% by weight of iron, calculated as $Fe_2O_3$, and up to 0.5% by weight of sulphur, calculated as elementary sulphur, and expressed relative to the anhydrous silicic acid.

The further preparation of the catalyst is then carried out by adding to the silicic acid described above vanadium, sulphur and at least one alkali metal in the elementary form or in the form of their compounds, such as hydroxides, oxides, sulphides, sulphates, oxalates and/or carbonates, the addition of these elements in the form of their compounds being preferred. Examples of vanadium compounds which may be mentioned are vanadium pentoxide, vanadyl sulphate and vanadyl oxalate. The vanadium compounds can be added in the solid form or in solution, for example as aqueous solutions or solutions in sulphuric acid, or in a suspended form. In a preferred embodiment, soluble salts of tetravalent vanadium, such as vanadyl sulphate, vanadyl oxalate or solutions of vanadyl oxalate in sulphuric acid are employed. Examples of possible sulphur compounds which may be mentioned are sulphuric acid, sulphides or salts of oxygen-acids of sulphur, such as sulphurous acid, sulphuric acid, pyrosulphuric acid and thiosulphuric acid. Examples which may be mentioned are sodium sulphite, potassium sulphite, lithium sulphate, sodium sulphide, potassium sulphide, sodium thiosulphate and potassium pyrosulphate.

Possible alkali metal compounds are all salts of the alkali metals, especially of lithium, of sodium and of potassium. In particular, salts of the oxygen-acids of sulphur, such as, for example, alkali metal sulphates, alkali metal bisulphates and alkali metal pyrosulphates, of carbonic acid and of organic carboxylic acid, such as formates, acetates, tartrates and oxalates, are preferred. The use of sodium sulphate, potassium sulphate and lithium sulphate is particularly preferred. The ratio of alkali metal to sulphur in the catalyst can vary within wide limits, the use of one to two equivalents of alkali metal per equivalent of sulphur having proved particularly suitable. The catalyst according to the invention in general contains 2 to 10% by weight of vanadium, 10 to 13% by weight of silicon, 5 to 15% by weight of sulphur, 5 to 20% by weight of potassium and 78 to 25% by weight of oxygen.

The catalyst can either contain only the elements vanadium, silicon, sulphur, potassium and oxygen, or also further elements. Examples of additional elements are magnesium, calcium, zinc, cadmium, barium, boron, aluminum, rare earths, titanium, zirconium, phosphorus, chromium, selenium, molybdenum, tellurium, tungsten, manganese, rhenium, iron, cobalt, nickel, ruthenium, rhodium, palladium, osmium, iridium and platinum. These elements are added to the remaining compounds when preparing the catalyst, either in the form of the elements or in the form of their compounds; in general, they are added in the form of the oxides, sulphates, oxalates, acetates, nitrates, tartrates, hydroxides, carbonates and/or acetylacetonates. Catalysts in which the sum of the contents of vanadium, silicon, sulphur, potassium and oxygen amounts to more than 95% by weight of the catalyst are preferred, and those in which this sum is 98 to 100% by weight are particularly preferred.

To prepare the catalyst, the procedure generally followed comprises uniformly admixing vanadium and/or a vanadium compound, sulfur and/or sulfur compound, an alkali metal compound and silicic acid of average particle size less than 50 micron and having an alkali metal content of less than 2% by weight, calculated as $Na_2O$ and expressed relative to anhydrous silicic acid. To prepare the catalyst the procedure can also be to mix the silicic acid with the sulfur compound, alkali metal compound or vanadium compound in question, and to achieve uniform distribution of silicic acid, alkali metal compound, vanadium compound and sulphur compound, this mixing is carried out in the presence of solvents, such as, for example, water or aqueous sulphuric acid. Thus, for example, the silicic acid can be mixed with solid potassium sulphate or an aqueous potassium sulphate solution or a solution of potassium sulphate in sulphuric acid. The point in time at which the vanadium compound is added is not critical; it may be added either to the silicic acid before adding the alkali metal compound, or after the addition of the alkali metal compound, or simultaneously. The use of sulphuric acid for preparing a soluble vanadium compound has in particular proved advantageous. Sulphuric acid is furthermore a suitable agent for arriving at the desired ratio of alkali metal to sulphur.

The catalyst mass thus obtained in general has a pasty consistency. It can be used either directly or after prior drying at temperatures of 50° to 200° C, preferably 100° to 150° C, or can, before being used as the catalyst, be subjected to a further treatment which is in itself known in the context of the preparation of catalysts. Thus it can in some cases be advantageous to employ the catalyst, not as a paste, but in a form with particular geometrical dimensions, such as spheres, cylindrical lengths or tablets. For this purpose, the catalyst paste obtained is dried, ground if necessary, and shaped mechanically, if appropriate after prior addition of lubricants, such as graphite. It can furthermore be advantageous to add compounds which can be decomposed thermally, such as ammonium carbonate, ammonium oxalate or oxalic acid, or compounds which decompose on treatment with oxygen-containing gases at an elevated temperature, such as for example, starch, in order thereby to influence the pore structure of the catalyst in a manner which is in itself known. The shaped catalyst can then, before being introduced into a reactor, furthermore be treated either by calcining or by heating to elevated temperatures, such as 200° to 400° C, whilst at the same time passing gases, such as air or nitrogen or carbon dioxide, over it. This treatment can, however, also be carried out in the subsequently used reactor for reacting organic compounds with oxygen, before the start of the reaction or in the course of the reaction. In this treatment, compounds which have entered the catalyst during the process of preparation, such as water, carbon, ammonium carbonate and/or oxalic acid, can be removed.

The catalyst according to the invention can be employed for the reaction of organic compounds with oxygen, for example for the oxidation of naphthalene to naphthoquinone, the oxidation of naphthalene or o-xylene to phthalic anhydride, the oxidation of toluene to benzaldehyde and the oxidation of benzene to hydroquinone. The use of the catalyst according to the invention in the preparation of naphthaquinone in accordance with the process of German published application No. 2,245,555 is particularly preferred. In this process, the reaction of naphthalene to naphthoquinone is carried out by passing a gas mixture consisting essentially of nitrogen, oxygen, water vapour, carbon dioxide and naphthalene under pressure at elevated temperature through a reactor in which there is a vanadium-containing catalyst in reaction tubes arranged in parallel. Suitable working conditions specified are pressures of 3 to 8 atmospheres, temperatures of 300°–400° C and initial concentrations of 1 to 5 mol % of naphthalene, 5 to 15 mol % of water, 1 to 15 mol % of carbon dioxide and 1 to 10 mol % of oxygen. The use of the catalyst according to the invention in this process gives improved values of the space-time yield and selectivity relative to naphthoquinone.

The invention is illustrated in the following examples.

EXAMPLES 1 TO 3

Catalysts A, B and C were prepared as follows:

EXAMPLE 1

Catalyst A (For comparison)

a. Preparation of a vanadyl sulphate solution (according to Fiat Report 649, London, 1947, pages 2–3).

2 kg of $V_2O_5$ in 5 liters of water and 2 kg of $H_2SO_4$ (96% strength) were heated to 70° C. $SO_2$ was passed in for 24 hours and the $V_2O_5$ is converted to a vanadyl sulphate solution. After cooling, the specific gravity was adjusted to 1.35 by adding water.

b. Preparation of a support.

75 l of a potassium silicate solution of 30° Bé, containing 94.5 kg of potassium silicate were mixed with 75 l of water; 112 kg of a 17% strength (16° Bé) $H_2SO_4$ were then added until the solution had a pH of 7. The precipitate was ground wet, and 2.2 l of a 25% strength solution of ammonia were added to the suspension of $SiO_2$, which is at pH 7, to give a pH value of 8.5 to 9.0. The precipitate was then filtered off. The filter cake was dried for 24 hours at 110°–120° C. The dry material was ground to a powder of average particle size 90 μu.

c. 5 kg of the support powder were introduced into ¼ of the above solution according to a) and the whole was converted to a paste by mixing for 30 minutes. The paste introduced into 5 mm diameter perforations in metal sheets of 5 mm thickness and dried for 2 hours at 50° C. The so formed tablets were then dried at 125° C and thereafter treated with air at 425° C for 12 hours.

EXAMPLE 2:

Catalyst B (according to the invention)

a. Preparation of a vanadyl sulphate solution. The procedure following was the same as with catalyst A.

b. Preparation of the support.

The procedure followed was the same with catalyst A, up to and including the addition of ammonia. Thereafter, however, the silicic acid was washed with water until it had an alkali content of 1% by weight, calculated as $Na_2O$ and expressed relative to anhydrous silicic acid. The silicic acid was then dried as for catalyst A and ground to a powder of average particle size 20 μu.

c. 2 kg of $K_2SO_4$, followed by 3 kg of silicic acid, were added to ¼ of the above solution according to (a) at 90° C and converted to a paste by mixing for 30 minutes at 90° C. The further preparation of the catalyst is carried out as for catalyst A.

EXAMPLE 3:

Catalyst C (according to the invention)

a. Preparation of a vanadyl sulphate solution.

4.7 kg of oxalic acid dihydrate were dissolved in 12.5 l of $H_2O$. 2 kg of $V_2O_5$ were added in portions, at 70° C. Thereafter, 4,4 kg of $H_2SO_4$ (96% strength) were added and the mixture was heated to the boil for 1 hour.

b. Preparation of the support.

The procedure followed was the same as for catalyst B, but starting from a sodium silicate solution instead of a potassium silicate solution.

c. The procedure followed was the same as with catalyst B, but the product was dried for 12 hours at 110° C, ground and then pressed, with addition of 10% by weight of graphite and 30% by weight of ammonium carbonate, to give 5 mm spheres. The spheres were heat-treated at 390° C for 24 hours.

EXAMPLES 4 TO 6

Naphthalene was reacted with oxygen in the presence of each of the catalysts A, B and C. The reaction was carried out in a steel reaction tube of 3 m length and 30 mm internal diameter, heated in a salt bath. 2 liters of catalyst were introduced into the reactor in each case. First a gas mixture of 94% of nitrogen and 6% of oxygen was passed over the catalyst at a rate of 4 normal cubic meters/hour at a pressure of 6 bars. The system was heated to 200° C and extra water was then added in an amount of 300 ml/hour. The system was then heated to 350° C and the catalyst was treated with the nitrogen-oxygen-water vapour mixture for 24 hours at this temperature and 6 bars. Thereafter, the system was cooled to a temperature of 320° C and gaseous naphthalene, in an amount of 690 g/hour, was then passed over the catalyst additionally to the mixture containing nitrogen, oxygen and water vapour. The temperature was then raised to 360° C at a rate of 6° C/hour. After the catalyst had been used for 1.000 hours, the following results were obtained:

| Example No. | Catalyst | g of naphtho-quinone/hour | g of phthalic anhydride/hour | % of converted naphthalene which has been converted to $CO_2$ |
|---|---|---|---|---|
| 4 | A | 98 | 90 | 1 |
| 5 | B | 120 | 100 | 1 |
| 6 | C | 134 | 103 | 0 |

Accordingly, improved values of the naphthoquinone space-time yield and selectivity are obtained with catalysts B and C.

What is claimed is:

1. Process for the catalytic oxidation of naphthalene to naphthoquinone comprising contacting naphthalene with molecular oxygen at an oxidizing reaction temperature in the presence of a fixed bed catalyst containing silicon, vanadium, sulfur, oxygen and at least one alkali metal element, said catalyst prepared from a silicic acid which has a water content between 0 and 20% by weight, has an average particle size of less than 50 microns and an alkali metal content of less than 2% by weight, calculated as $Na_2O$ and expressed relative to anhydrous silicic acid.

2. Process of claim 1 wherein the oxidation is effected at a pressure of from 3 to 8 atmospheres, a temperature of from 300°–400° C and in the presence of water vapor and carbon dioxide.

3. A process according to claim 1 wherein the catalyst contains from 2 to 10% by weight vanadium, from 10 to 13% by weight of silicon, from 5 to 15% by weight of sulfur, from 5 to 20% by weight of potassium and from 25 to 78% by weight of oxygen.

4. A process according to claim 1 wherein the sum of the contents of vanadium, silicon, sulfur, potassium and oxygen is more than 95% by weight of the catalyst.

5. A process according to claim 1 wherein the silicic acid has an average particle size of from 10 to 30 microns.

6. A process according to claim 1 wherein the silicic acid has an internal surface area (as determined by the BET method) of from 100 to 200 $m^2/g$.

7. A process according to claim 1 wherein the catalyst contains from 1 to 2 equivalents of alkali metal per equivalent of sulfur.

8. A process according to claim 1 wherein the catalyst is prepared by a process comprising uniformly admixing vanadium and/or vanadium compound, sulfur and/or a sulfur compound, an alkali metal compound and silicic acid of average particle size less than 50 microns and having an alkali metal content of less than 2% by weight, calculated as $Na_2O$ and expressed relative to anhydrous silicic acid.

9. A process according to claim 8 wherein the vanadium is present in the mixture employed to form the catalyst as vanadium hydroxide, oxide, sulfate, oxalate and/or carbonate.

10. A process according to claim 9 wherein the vanadium is present in the mixture as vanadium oxalate, in the form of an aqueous solution containing sulfuric acid.

* * * * *